United States Patent
Anand et al.

(10) Patent No.: US 7,060,471 B2
(45) Date of Patent: Jun. 13, 2006

(54) STEREOSELECTIVE CHEMOENZYMATIC PROCESS FOR THE PREPARATION OF OPTICALLY ENRICHED PHENYLGLYCIDATES AS PRECURSORS OF TAXOL SIDE CHAIN

(75) Inventors: Naveen Anand, Jammu (IN); Munish Kapoor, Jammu (IN); Subhash Chandra Taneja, Jammu (IN); Surrinder Koul, Jammu (IN); Rattan Lal Sharma, Jammu (IN); Ghulam Nabi Qazi, Jammu (IN)

(73) Assignee: Council of Scientific & Industrial Research, New Delhi (IN)

( * ) Notice: Subject to any disclaimer, the term of this patent is extended or adjusted under 35 U.S.C. 154(b) by 66 days.

(21) Appl. No.: 10/798,199

(22) Filed: Mar. 10, 2004

(65) Prior Publication Data

US 2004/0259943 A1  Dec. 23, 2004

(30) Foreign Application Priority Data

Mar. 12, 2003  (IN) ................................ 275/Del/03

(51) Int. Cl.
*C12P 17/02*  (2006.01)
*C07D 301/26*  (2006.01)

(52) U.S. Cl. ........................ 435/123; 549/514; 549/549

(58) Field of Classification Search ................ 549/514, 549/549, 555; 435/123
See application file for complete search history.

(56) References Cited

U.S. PATENT DOCUMENTS 6,020,174 A * 2/2000 Chen et al. .................. 435/123

* cited by examiner

*Primary Examiner*—Bernard Dentz
(74) *Attorney, Agent, or Firm*—Merchant & Gould P.C.

(57) ABSTRACT

The present invention relates to a novel and efficient chemoenzymatic process of preparation of optically active trans alkyl phenylglycidates. The invention particularly discloses a novel process for the chemoenzymatic synthesis of two enantiomers of trans alkyl phenylglycidate i.e. alkyl(2S, 3R)-phenylglycidate and alkyl(2R,3S)-phenylglycidate of formulae 7 and 8 respectively

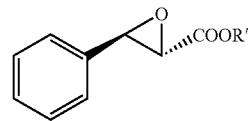

(2S, 3R)     (7)

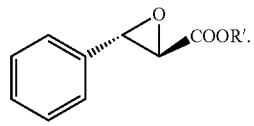

(2R, 3S)     (8)

20 Claims, No Drawings

STEREOSELECTIVE CHEMOENZYMATIC PROCESS FOR THE PREPARATION OF OPTICALLY ENRICHED PHENYLGLYCIDATES AS PRECURSORS OF TAXOL SIDE CHAIN

FIELD OF INVENTION

The present invention relates to a novel and efficient chemoenzymatic process of preparation of optically active trans alkyl phenylglycidates. The invention particularly discloses a novel process for the chemoenzymatic synthesis of two enantiomers of trans alkyl phenylglycidate i.e. alkyl(2S, 3R)-phenylglycidate and alkyl(2R,3S)-phenylglycidate of formulae 7 and 8 respectively.

BACKGROUND AND PRIOR ART REFERENCES

Optically enriched alkyl(2S,3R)-phenylglycidate and alkyl(2R,3S)-phenyl-glycidate of formulae 7 and 8 are the key intermediates used in the synthesis of N-benzoyl-(2R, 3S)-3-phenylisoserine (Taxol side chain). Paclitaxel or Taxol which was isolated from the bark of the Pacific Yew (*Taxus brevifolia*)(Wani et al *J Am Chem Soc.* 93, 2325–7 1971) and has been approved for the treatment of

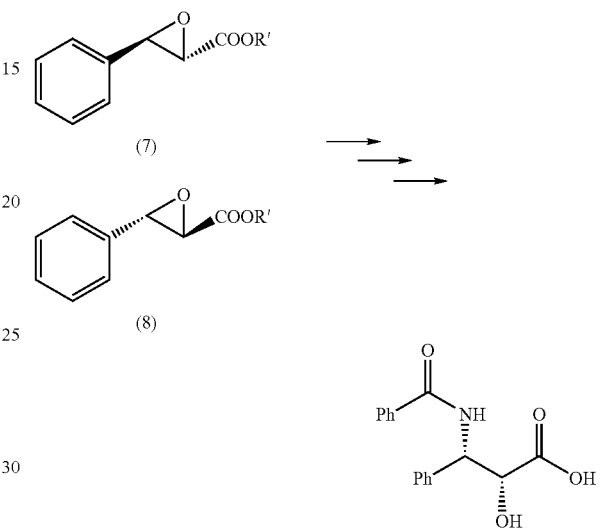

Taxol

10-Deacetyl baccatin-III

Isoserine various types of cancers(Holmes et al *J. Natl. Cancer Inst.* 83, 1797–1805,1991).

Despite being one of the most promising anti-cancer drugs, its very low occurrence (40–165 mg/kg) in nature is the main hindrance in its production. Fortunately it has been found that 10-deacetyl baccatin-III which is structurally closely related to Taxol and occurs in comparatively higher concentrations (approx. 1 g/kg), can be easily isolated from fresh leaves of European Yew (*Taxus baccata*). It is also reported that Paclitaxel is 1000 times more potent compared to 10-deacetyl baccatin-III and its higher activity is due to a C-13 side chain comprising N-benzoyl-(2R,3S)-3-phenylisoserine moiety (Wani et al *J Am Chem Soc.* 93, 2325–7 1971).

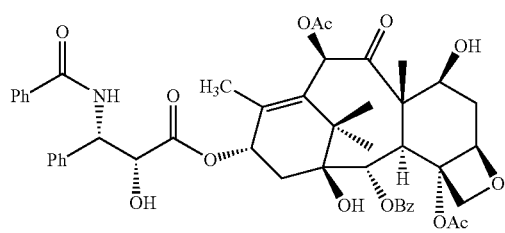

(7)

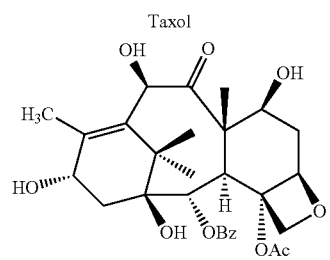

(8)

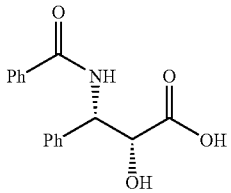

Therefore synthesis of optically active (2S,3R) and (2R, 3S)-phenylglycidates of formula 7 and 8 which are the key chiral precursors for synthesising N-benzoyl-(2R,3S)-3-phenylisoserine has become very vital for the development of a practical and efficient route to synthesise enantiomerically pure isoserine chain.

There are number of reports on the preparation of these chiral intermediates by biochemical or chemoenzymatic methods besides asymmetric syntheses. Most of these reports are related to kinetic resolution of racemic 2-halo-3-hydroxy-3-phenylpropanoate through enzymatic hydrolysis (H. Honig et al., *Tetrahedron* 46, 3841–3850, 1990; Peter G. M Wuts et al, *Tetrahedron Asymmetry* 11, 2117–2123, 2000), or by transesterification reaction (Ching-Shih Chen et al., *J. Org. Chem.* 58, 1287–1289, 1993; Ching-Shih Chen et al., U.S. Pat. No. 6,020,174, to The Board of Governors for Higher Education, Rhodes Island; Marco Villa et al., U.S. Pat. No. 6,187,936 to Zambon Group S.p.A; Tanebe JP 06/078790) or via resolution of azetidinones (C. J Sih et al., *J. Org. Chem.* 58, 1068–1075, 1993; R. N. Patel et al, *J. American Oil Chemists Society*, 73, 1363–1375, 1996; R. A. Holton et al, WO 2001029245, EP 1222305 to Bristol-Myers Squibb; R. N. Patel et al., *Biotechnology and Applied Biochemistry*, 20, 23–33, 1994).

From the literature review it is quite clear that no prior art is available on kinetic resolution of racemic 2-halo-3-hydroxy-3-phenylpropanoates where x represents bromo and iodo groups and R' represents C-1 to C-5 alky group. Therefore the use of bromo and iodohydrins via kinetic resolution route for the preparation of desired (2S,3R) and (2R,3S)-phenylglycidates in essentially novel and has not been reported in the literature or known in the art of their synthesis of taxol side chain precursors.

The present invention therefore discloses the application of a lipase for the preparation of (2S,3R) and (2R,3S)-phenylglycidates via kinetic resolution of halohydrin intermediates x and R' are defined as above.

OBJECTS OF THE INVENTION

Thus the main objective of the present invention is to synthesise optically active alkyl(2S,3R) and (2R,3S)-phenylglycidates of formulae 7 and 8 using chemoenzymatic approach through resolution of its racemic precursor trans alkyl 2-halo-3-hydroxy-3-phenylpropanoates of formula 2 where x represents bromine or iodine and R' represents C-1 to C-5 alkyl group. Advantage of using bromo and iodohydrin intermediates are that they are easily preparable in almost quantitative yields and are obtained in crystalline form. Moreover these compounds can be easily converted to corresponding epoxides (glycidates) by acid and base catalysed transformations in almost quantitative yields. Additionally use of lipase from *Aspergillus niger* makes the process of resolution of trans alkyl 2-halo-3-hydroxy-3-phenylpropanoates facile.

SUMMARY OF THE INVENTION

The present invention relates to a novel and efficient chemoenzymatic process of preparation of optically active trans alkyl phenylglycidates. The invention particularly discloses a novel process for the chemoenzymatic synthesis of two enantiomers of trans alkyl phenylglycidate i.e. alkyl(2S,3R)-phenylglycidate and alkyl(2R,3S)-phenylglycidate of formulae 7 and 8 respectively. process of their synthesis comprises cohalogenation reaction of alkyl cinnamate of formula 1 where R' represents C-1 to C-5 alkyl group to form trans 2-halo-3-hydroxy-3-phenylpropanoates of formula 2 where x represents Br or I, then converting the halohydrins of formula 2 to corresponding alkyl acylates of formula 3 where x and R' represents as above, subsequently incubating the acyl derivatives of alkyl 2-halo-3-hydroxy-3-phenylpropanoates of formula 3 with crude dry powder of lipase from *Aspergillus niger* in an aqueous buffer phase in presence of an organic solvent, thereafter separating the hydrolysed halohydrins i.e. alkyl(2R,3R) 2-halo-3-hydroxy-3-phenylpropanoates of formula 4 and unhydrolysed ester i.e. alkyl(2S,3S) 2-halo-3-acyloxy-3-phenylpropanoates of formula 5 from the mixture by conventional method, if required then again incubating the optically enriched acyl derivatives of formula 5 with crude dry powder of lipase from *Aspergillus niger* in an aqueous buffer phase in presence of an organic solvent to further improve the enantiopurity, followed by reaction of the optically enriched products of formula 5 with an acid to furnish optically enriched alkyl(2S,3S) 2-halo-3-hydroxy-3-phenylpropanoate of formula 6 and finally treating the compounds of formulae 4 and 6 with an alkali in an organic or aqueous phase to furnish optically enriched alkyl(2S,3R)-phenylglycidate and alkyl (2R,3S)-phenylglycidate of formulae 7 and 8 respectively.

Use of lipase from *Aspergillus niger* for the kinetic resolution of trans alkyl 2-halo-3-hydroxy-3-phenylpropanoates where x and R' represents as above is novel as also the step of acid followed by a base catalysed reaction for the cyclisation of resolved esters of trans alkyl 2-halo-3-hydroxy-3-phenylpropanoates of formula 4 and 6, not reported in the art of its synthesis.

DETAILED DESCRIPTION OF THE INVENTION

Accordingly the present invention relates to the synthesis of a stereoselective chemoenzymatic process for the synthesis of optically enriched trans alkyl phenylglycidate in its enantiomeric forms alkyl(2S,3R)-phenylglycidate and alkyl (2R,3S)-phenylglycidate of formulae 7 and 8

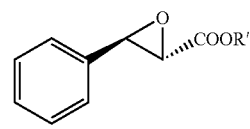

(2S, 3R)

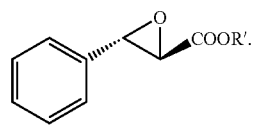

(2R, 3S)

respectively, wherein said process comprises steps of, a. halogenating halohydrins of formula 2, where x represents bromine or iodine, and R' represents C-1 to C-5 alkyl group from corresponding alkyl cinnamates of formula 1 by action of a halogenating agent;

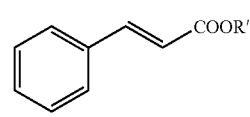

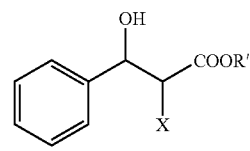

b. acylating the halohydrins of formula 2 using an acyl anhydride in presence of a base to trans alkyl 3-acyloxy-2-halo-3-phenylpropanoates of formula 3;

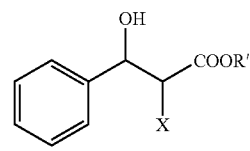

c. incubating the trans alkyl 3-acyloxy-2-halo-3-phenylpropanoates of formula 3 with dry powder of the lipase in an aqueous buffer phase optionally in presence of an organic medium at a temperature range of 10–40° C. for the time duration in the range of 30–55 hr. to facilitate the reaction to get hydrolysed alkyl(2R,3R)-2-halo-3-hydroxy-3-phenylpropanoates of formula 4 and unhydrolysed alkyl(2S, 3S)-3-acyloxy-2-halo-3-phenylpropanoates of formula 5;

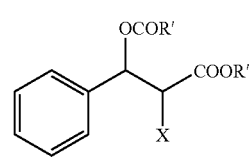

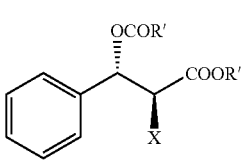

(5)

d. separating the hydrolysed alkyl(2R,3R)-2-halo-3-hydroxy-3-phenylpropanoates of formula 4 and unhydrolysed alkyl(2S,3S)-3-acyloxy-2-halo-3-phenylpropanoates of formula 5 by conventional method of chromatography.
e. incubating the optically enriched unhydrolised phenyl proponoates of formula 5 with crude dry powder of lipase from *Aspergillus niger* in an aqueous buffer phase in presence of an organic solvent to further improve the enantiopurity;
f. reacting the optically enriched products of formula 5 with an acid to furnish optically enriched alkyl(2S,3S) 2-halo-3-hydroxy-3-phenylpropanoate of formula 6, and

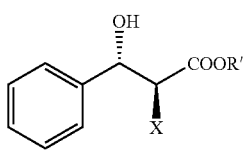

(6)

g. treating the compounds of formulae 4 and 6 with an alkali in an organic or aqueous phase which leads the formation of epoxide ring by cyclisation to furnish optically enriched alkyl(2S,3R)-phenylglycidate and alkyl(2R,3S)-phenylglycidate of formulae 7 and 8 respectively.

In a preferred embodiment of the process of preparation of halohydrins from alkyl cinnamates of formula 1 to halohydrins of formula 2 in step 'a' of the process, the halogenating agent is selected from N-halosuccinimide such as N-bromosuccinimide, N-iodosuccinimide or sodium bromate, periodic acid, 1,3-dibromo-5,5-dimethyl hydantoin, iodine, bromine but more preferably sodium bromate for bromohydroxylation or periodic acid for iodohydroxylation in an aqueous phase or in a mixed organic aqueous phase where organic solvent may be selected from water miscible solvents such as acetone, tetrahydrofuran, dioxane, acetonitrile.

In another embodiment the formation of halohydrins is carried out at a temperature in the range of 0–60° C. more preferably at 30–40° C.

In yet another embodiment in step 'b' of the transformation of compound of formula 2 to acylate of formula 3, the acylating agent is selected from acyl anhydrides such as acetic anhydride; propionic anhydride and butyric anhydride or corresponding acyl chlorides but most suitable is acetic anhydride in presence of bases like pyridine, N,N-dimethyl aminopyridine (DMAP) and more preferably DMAP.

In yet another embodiment in step 'c' of the process of kinetic resolution of the compound of formula 3 is effected by incubating the compound of formula 3 in presence of crude lipase enzyme (AS AMANO) from *Aspergillus niger* either in a buffered aqueous phase alone or a buffered aqueous phase in presence of an organic medium as a cosolvent which facilitates the hydrolytic reaction. The pH of the buffer is suitably adjusted at 5–7.5, more suitably at 6–7.5 and most suitably at 7.

In still yet another embodiment the temperature of the reaction is selected at 10–40° C., but more suitably at 20–35° C. and most suitably at 30° C.

In yet another embodiment the incubation period is about 48 hr.

In another feature the preferred aqueous phase is water, phosphate buffer (0.1M to 0.2M) or an acetate buffer and the most preferred one is phosphate buffer (0.1M). The preferred cosolvents that are added in the ratio of 10–90% are hexane, toluene, dichloromethane, acetone, acetonitrile, dimethylformamide, dimethyl sulphoxide, methanol, ethanol and the like. The more preferable are toluene, acetone and acetonitrile and most preferable is acetonitrile.

In another embodiment after the completion of the hydrolysis reaction in step 'd' of the process the separation of hydrolysed alcohol of formula 4 and unhydrolysed ester of formula 5 is effected by column chromatography on silica gel columns by conventional chromatographic methods.

In yet another embodiment in step 'e' of the process of base catalysed conversion of the compound of the formula 4 (hydrolysed ester) to alkyl(2S,3R)-phenylglycidates of the formula 7, is effected by an inorganic or organic base such as sodium hydroxide, sodium carbonate and the like and organic bases are selected from triethylamine, piperidine, 1,4-diazabicyclo[2,2,2]octane (DABCO), 1,8-diazabicyclo[5,4,0]undec-7-ene (DBU) and the like, the more preferred base is DBU.

In still another embodiment in step 'f' of the process of acid catalysed conversion of the compound alkyl(2S,3S)-3-acyloxy-2-halo-3-phenylpropanoates of the formula 5 (unhydrolysed ester) first to alkyl(2S,3S)-2-halo-3-hydroxy-3-phenylpropandates of formula 6 is effected by mineral acid such as hydrochloric acid, sulfuric acid or an organic or lewis acid such as trifluoro acetic acid, boron trifluoride (BF$_3$) in an organic solvent such as diethyl ether, methanol, acetone and the like but the preferred acidic conditions are 1N, 2N and 5N HCl, most preferred is 2N HCl in methanol, finally transformation to alkyl(2R,3S)-phenylglycidates of the formula 8 is effected by a base as described in step 'e".

The invention is described herein with reference to the examples given below. These examples should not be construed as to restrict the scope of this invention.

Step 'a'

EXAMPLE (i)

Synthesis of (±)-methyl 2-bromo-3-hydroxy-3-phenylpropanoate of formula 2 where x=Br and R'=CH$_3$ Potassium bromate (4 g, 24 mmol), was dissolved in 40 ml water and adjusted to pH 1–2 with 2M H$_2$SO$_4$. To the resultant solution was added methyl cinnamate (3 g, 20 mmol) in 40 ml acetonitrile. 1M sodium bisulphite solution (5.2 g in 50 ml) was added to the above mixture over a period of two hours with stirring and at 40° C. The reaction mixture was further stirred for 36 hrs till the reaction was complete (TLC monitored). The resulting solution was extracted with ethyl acetate (3×100 ml), and combined organic layer was washed with aqueous sodium sulphite followed by drying over anhydrous sodium sulphate. The contents concentrated in vacuo to give a crude material, which was purified by crystallization (benzene:hexane, 1:1) to furnish compound of formula 2 m.pt 63° C. (yield 70%).

$^1$HNMR (CDCl$_3$) δ: 7.37(5H, s, Ar—H), 5.08(1H, d, J=8.25 Hz, CH—OH), 4.38(1H, d, J=8.24 Hz, CH—Br), 3.80(3H, s, COOCH$_3$).

EXAMPLE (ii)

Synthesis of (±)-ethyl
2-bromo-3-hydroxy-3-phenylpropanoate of formula
2 where x=Br and R'=C$_2$H$_5$ It was prepared from ethyl cinnamate (3.26 g, 20 mmol) potassium bromate (4 g, 24 mmol) following the procedure given in example step 'a' (i), m.pt 76–77° C., yield 3.7 g, (70%).
$^1$HNMR(CDCl$_3$) δ: 7.38(5H, s, Ar—H), 5.08(1H, d, J=8.29 Hz, CH—OH), 4.54(1H, d, J=8.28 Hz, CH—Br), 4.25(2H, q, J=7.11 Hz, CH$_2$), 1.25(3H, t, J=7.12 Hz CH$_3$).

EXAMPLE (iii)

Synthesis of (±)-methyl
3-hydroxy-2-iodo-3-phenylpropanoate of formula 2
where x=I and R'=CH$_3$ To a stirred suspension of methyl cinnamate(3g, 20 mmol), HIO$_4$.2H$_2$O (5.2 g, 24 mmol) 12 ml water and 40 ml of acetonitrile, 1M sodium bisulphite solution (5.2 g in 50 ml) was added to the above mixture over a period of three-four hours with stirring and at 30° C. The reaction mixture was further stirred for 36 hrs till the reaction was complete (TLC monitored). The resulting solution was extracted with ethyl acetate (3×50 ml), and combined organic layer was washed with aqueous sodium sulphite followed by drying over anhydrous sodium sulphate. The contents concentrated in vacuo to give a crude material, which was purified by crystallization (benzene:hexane, 1:1) to furnish compound of formula 2 m.pt 63° C., yield 3g (65%).
$^1$HNMR(CDCl$_3$) δ: 7.35(5H, s, Ar—H), 5.05(1H, d, J=8.42 Hz, CH—OH), 4.55(1H, d, J=8.43 Hz, CH—Br), 3.75(3H, s, CH$_3$).

EXAMPLE (iv)

Synthesis of (±)-ethyl
3-hydroxy-2-iodo-3-phenylpropanoate of formula 2
where x=I and R'=C$_2$H$_5$ It was prepared from ethyl cinnamate.(3.26 g, 20 mmol), HIO$_4$.2H$_2$O (5.2 g, 24 mmol) following the procedure given in example step 'a' (iii), yield 4 g (77%), m.pt 79° C.
$^1$HNMR(CDCl$_3$) δ: 7.38(5H, s, Ar—H), 5.05(1H, d, J=8.29 Hz, CH—OH), 4.55(1H, d, J=8.29 Hz, CH—Br), 4.25(2H, q, J=7.11 Hz, CH), 1.25(3H, t, J=7.12 Hz, CH$_2$CH$_3$).

Step 'b'

EXAMPLE (i)

Synthesis of (±)-methyl
3-acetoxy-2-bromo-3-phenylpropanoate of formula
3 where x=Br and R'=CH$_3$ A solution of 2 (2.59 g, 10 mmol) and acetic anhydride (12mmol) and dimethyl N,N-dimethyl aminopyridine (DMAP) (in catalytic amount) in 10 ml of dry dichloromethane was kept overnight at room temp. The reaction mixture was poured into ice-cold water and extracted with dichloromethane (3×100 ml). The organic layer was washed, dried, and evaporated to furnish compound of formula 3, which was purified by column chromatography (silica gel, ethyl acetate:hexane; 3:97), in 90–95% yield, m.pt. 56° C.
$^1$HNMR (CDCl$_3$)δ: 7.45(5H, s, Ar—H), 6.23(1H, d, J=10.00 Hz, CH—OAc), 4.58(1H, d, J=10.00 Hz, CH—Br), 3.83(3H, s, COOCH$_3$), 2.03(3H, s, OCOCH$_3$).

EXAMPLE (ii)

Synthesis of (±)-ethyl
3-acetoxy-2-bromo-3-phenylpropanoate of formula
3 where x=Br and R'=C$_2$H$_5$ It was prepared from 2 (2.73 g, 10 mmol) and acetic anhydride (12 mmol) and N,N-dimethyl aminopyridine (DMAP), in catalytic amount) following the procedure given in step 'b' example (i) in 90–95% yield.
$^1$HNMR (CDCl$_3$)δ: 7.50(5H, s, Ar—H), 6.23(1H, d, J=10.50 Hz, CH—OAc), 4.53(1H, d, J=10.50 Hz, CH—Br), 4.33(2H, q, J=7.11 Hz CH$_2$), 2.06(3H, s, OCCCH$_3$), 1.33 (3H, t, J=7.12 Hz CH$_2$CH$_3$).

EXAMPLE (iii)

Synthesis of (±)-methyl
3-acetoxy-2-iodo-3-phenylpropanoate of formula 3
where x=I and R'=CH$_3$ It was prepared from 2 (3.06 g, 10 mmol) and acetic anhydride (12 mmol) and N,N-dimethyl aminopyridine (DMAP), in catalytic amount) following the procedure given in step 'b' example (i) in 90–95% yield, m.pt, 58° C.
$^1$HNMR(CDCl$_3$) δ: 7.40(5H, s, Ar—H), 6.15(1H, d, J=10.75 Hz, CH—OAc), 4.62(1H, d, J=10.75 Hz, CH—Br), 3.17(3H, s, COOCH$_2$), 2.00(3H, s, CH$_3$).

EXAMPLE (iv)

Synthesis of (±)-ethyl
3-acetoxy-2-iodo-3-phenylpropanoate of formula 3
where x=I and R'=C$_2$H$_5$ It was prepared from 2 (3.19 g, 10 mmol) and acetic anhydride (12 mmol) and N,N-dimethyl aminopyridine (DMAP), in catalytic amount) following the procedure given in step 'b' example (i) in 90–95% yield.
$^1$HNMR(CDCl$_3$) δ: 7.50(5H, s, Ar—H), 6.15(1H, d, J=10.50 Hz, CH—OAc), 4.62(1H, d, J=10.50 Hz, CH—Br), 4.25(2H, q, J=7.11 Hz COOCH$_2$), 2.06(3H, s, OCOCH$_3$), 1.25(3H, t, J=7.12 Hz CH$_2$CH$_3$).

Step 'c'

EXAMPLE (i)

Preparation of (−)-methyl(2R,3R)-2-bromo-3-hydroxy-3-phenylpropanoate of formula 4 by kinetic resolution, where x=Br and R'=CH$_3$ (±)-Methyl 3-acetoxy-2-bromo-3-phenylpropanoate (800 mg) of formula 3 where x=Br and R'=CH$_3$, was added to biphasic system of aqueous phosphate buffer (16 ml, 0.1M. pH 7.0) and toluene (1.6 ml). To the above solution was added crude dry powder of lipase *Aspergillus niger* (Amano AS, 400 mg, 12–15 units/mg) with the continuous stirring and maintaining pH 7.0 by addition of 0.5N sodium hydroxide solution. During the course of the reaction temperature was maintained at 30° C. The progress of the reaction was monitored after every six hours by TLC and HPLC. After completion of the reaction (48 hrs., approx., 43% conversion), the reaction was terminated by centrifuging the mixture at 10,000 to 15,000 g to remove enzyme and the suspended particles. The clear solution and the centrifuged mass was extracted separately with ethyl acetate (3×20 ml). The organic layer was combined and washed with water. The combined solvent layer was then dried and evaporated under reduced pressure to furnish a mixture comprising hydrolysed alcohol and unhydrolysed ester which were separated by column chromatography over silica gel using hexane:ethyl acetate (97:3) as eluent to furnish (−)-methyl(2R,3R)-2-bromo-3-hydroxy-3-phenylpropanoate of formula 4 (250 mg, 85%) having enantiomeric purity (EE)92%, $[\ ]_D^{25}$−19.7° (c,l,CHCl$_3$) and unhydrolysed ester (+)-methyl(2S, 3S)-3-acetoxy-2-bromo-3-phenylpropanoate of formula 5 (378 mg, 83%) having enantiomeric purity (EE)70% (chiral HPLC), $[\ ]_D^{25}$+36.4° (c,l,CHCl$_3$).

EXAMPLE (ii)

Preparation of (−)-ethyl(2R,3R)-2-bromo-3-hydroxy-3-phenylpropanoate of formula 4 by kinetic resolution, where x=Br and R'=C$_2$H$_5$ It was prepared from (±)-ethyl 3-acetoxy-2-bromo-3-phenylpropanoate (800 mg) of formula 3, phosphate buffer (16 ml, 0.1M. pH 7.0), toluene (1.6 ml) and crude dry powder of lipase *Aspergillus niger* (Amano AS, 400 mg, 12–15 units/mg) following the procedure given in step 'c' example (i). After 48 hrs. (45% conversion) the hydrolyzed alcohol was obtained (256 mg, 82%), having enantiomeric purity (EE) 86%, $[\ ]_D^{25}$−14.8° (c,l,CHCl$_3$) and unhydrolysed ester (+)-ethyl(2S,3S)-3-acetoxy-2-bromo-3-phenylpropanoate of formula 5 (375 mg, 85%) having enantiomeric purity (EE)73%(chiral HPLC), $[\ ]_D^{25}$+37.5° (c,l,CHCl$_3$).

EXAMPLE (iii)

Preparation of (−)-methyl(2R,3R)-3-hydroxy-2-iodo-3-phenylpropanoate of formula 4 by kinetic resolution, where x=I and R'=CH$_3$ It was prepared from (+)-Methyl 3-acetoxy-2-iodo-3-phenylpropanoate (800 mg) of formula 3, phosphate buffer (16 ml, 0.1M. pH 7.0), toluene (1.6 ml) and crude dry powder of lipase *Aspergillus niger* (Amano AS, 400 mg, 12–15 units/mg) following the procedure given in step 'c' example (i). After 36 hrs. (44% conversion) the hydrolyzed alcohol was obtained (274 mg, 88%), having enantiomeric purity (EE) 94%, $[\ ]_D^{25}$ 0.0° (c,l,CHCl$_3$); −3.0° (c,l, MeOH) and unhydrolysed ester (+)-methyl-(2S,3S)-3-acetoxy-2-iodo-3-phenylpropanoate of formula 5 (415 mg, 92%) having enantiomeric purity (EE)76%(chiral HPLC), $[\ ]_D^{25}$+48.0° (c,l,CHCl$_3$).

EXAMPLE (iv)

Preparation of (−)-ethyl(2R,3R)-3-hydroxy-2-iodo-3-phenylpropanoate of formula 4 by kinetic resolution, where x=I and R'=C$_2$H$_5$ It was prepared from (±)-Ethyl 3-acetoxy-2-iodo-3-phenylpropanoate (800 mg) of formula 3, phosphate buffer (16 ml, 0.1M. pH 7.0), toluene (1.6 ml) and crude dry powder of lipase *Aspergillus niger* (Amano AS, 400 mg, 12–15 units/mg) following the procedure given in step 'c' example (i). After 40 hrs. (40% conversion) the hydrolyzed alcohol was obtained (250 mg, 88%), having enantiomeric purity(EE) 95%, $[\ ]_D^{25}$−9.3° (c,l,CHCl$_3$) and unhydrolysed ester (+)-ethyl(2S,3S)-3-acetoxy-2-iodo-3-phenylpropanoate of formula 5 (440 mg, 91%) having enantiomeric purity (EE)60% (chiral HPLC), $[\ ]_D^{25}$+36.0° (c,l,CHCl$_3$).

EXAMPLE (v)

Preparation of (+)-methyl(2S,3S)-3-acetoxy-2-bromo-3-phenylpropanoate of formula 5 by double kinetic resolution, where x=Br and R'=CH$_3$ It was prepared from optically enriched (+)-Methyl(2S,3S)-3-acetoxy-2-bromo-3-phenylpropanoate (EE, 70%, 350 mg) of formula 5, phosphate buffer (7 ml, 0.1M. pH 7.0), toluene (0.7 ml) and crude dry powder of lipase *Aspergillus niger* (Amano AS, 100 mg, 12–15 units/mg) following the procedure given in step 'c' example (i), After completion of the reaction (72 hrs.), the unhydrolyzed ester on separation (290 mg) was found to have enantiomeric excess (EE)>99% (chiral HPLC), $[\ ]_D^{25}$+52.0° (c,l, CHCl$_3$).

EXAMPLE (vi)

Preparation of (+)-ethyl(2S,3S)-3-acetoxy-2-bromo-3-phenylpropanoate of formula 5 by double kinetic resolution, where x=Br and R'=C$_2$H$_5$ It was prepared from optically enriched ethyl(2S,3S)-3-acetoxy-2-bromo-3-phenylpropanoate (EE 73%, 350 mg) of formula 3, phosphate buffer (7 ml, 0.1M. pH 7.0), toluene (0.7 ml) and crude dry powder of lipase *Aspergillus niger* (Amano AS, 100 mg, 12–15 units/mg) following the procedure given in step 'c' example (i). After 65 hrs the unhydrolyzed ester on separation (290 mg) was found to have enantiomeric excess (EE)98%(chiral HPLC), $[\ ]_D^{25}$+50.5° (c,l, CHCl$_3$).

EXAMPLE (vii)

Preparation of (+)-methyl(2S,3S)-3-acetoxy-2-iodo-3-phenylpropanoate of formula 5 by double kinetic resolution, where x=I and R'=CH$_3$ It was prepared from optically enriched methyl(2S,3S)-3-acetoxy-2-iodo-3-phenylpropanoate (EE 76%, 350 mg) of formula 3, phosphate buffer (7 ml, 0.1M. pH 7.0), toluene (0.7 ml) and crude dry powder of lipase *Aspergillus niger* (Amano AS, 100 mg, 12–15 units/mg) following the procedure given in step 'c' example (i). The unhydrolyzed ester of formula 5 (300 mg) was found to have enantiomeric excess (EE)94%(chiral HPLC), $[\ ]_D^{25}$+59.0° (c,l, CHCl$_3$).

EXAMPLE (viii)

Preparation of (+)-ethyl(2S,3S)-3-acetoxy-2-iodo-3-phenylpropanoate of formula 5 by double kinetic resolution, where x=I and R'=C$_2$H$_5$ It was prepared from optically enriched methyl(2S,3S)-3-acetoxy-2-iodo-3-phenylpropanoate (EE 60%, 350 mg) of formula 3, phosphate buffer (7 ml, 0.1M. pH 7.0), toluene (0.7 ml) and crude dry powder of lipase *Aspergillus niger*

Amano AS (100 mg, 12–15 units/mg) The unhydrolyzed ester (315 mg)(72 hrs.) was found to have enantiomeric excess (EE)73%(chiral HPLC), [ ]$_D^{25}$+43.5° (c,l, CHCl$_3$).

EXAMPLE (ix)

Preparation of (−)-methyl(2R,3R)-2-iodo-3-hydroxy-3-phenylpropanoate of formula 4 by kinetic resolution in presence of a cosolvent acetonitrile, where x=I and R'=CH$_3$ (+)-Methyl 3-acetoxy-2-iodo-3-phenylpropanoate (200 mg) of formula 3 was added to biphasic system of aqueous phosphate buffer (3.6 ml, 0.1M. pH 7.0) and acetonitrile (0.4 ml). To the above solution crude dry powder of lipase *Aspergillus niger* (Amano AS, 100 mg, 12–15 units/mg) was added with the continuous stirring and maintaining pH 7.0 by addition of 0.5N sodium hydroxide solution. During the course of the reaction temperature was maintained at 30° C. The progress of the reaction was monitored after every six hours. After the completion of the reaction (9 hrs., approx., 43% conversion), the reaction was terminated by centrifuging the mixture at 10,000 to 15,000g to remove enzyme and the suspended particles. The clear solution and the centrifuged mass was extracted separately with ethyl acetate (3×30 ml). The organic layer was combined and washed with water. The combined solvent layer was then dried and evaporated under reduced pressure to furnish a mixture comprising hydrolysed alcohol and unhydrolysed ester which were separated by column chromatography over silica gel using hexane:ethyl acetate (97:3) as eluent to furnish methyl(2R,3R)-3-hydroxy-2-iodo-3-phenylpropanoate of formula 4 (65 mg, 85%) having enantiomeric purity (EE) 92% and unhydrolysed ester methyl(2S,3S)-3-acetoxy-2-iodo-3-phenylpropanoate of formula 5 (92 mg, 77%), enantiopurity (EE) 62% determined by chiral HPLC.

Step 'e'

EXAMPLE (i)

Preparation of (+)-methyl(2S,3R)-phenylglycidate of the formula 7 where R'=CH$_3$ 0.2 ml of 1,8-diazabicyclo[5,4,0]undec-7-ene (DBU) was added to a solution of optically enriched halohydrin (200 mg) of formula 4 in methanol (4 ml) at 20° C. for 5 minutes. The solvent was removed under reduced pressure and the reaction mixture was diluted with 10 ml water and extracted with ethyl acetate and solvent removed to furnish compound of formula 7; recovery 98 mg, [ ]$_D^{25}$+155.0° (c,l, CHCl$_3$)

Step 'f'

EXAMPLE (i)

Preparation of (+)-methyl(2S,3S)-2-halo-3-hydroxy-3-phenylpropanoate of formula 6 where R'=CH$_3$ Alkyl(2S,3S)-3-acetoxy-2-holo-3-phenylpropanoate of formula 5 (200 mg) was dissolved in 4 ml of methanol and 0.2 ml of 2N HCl was added and the reaction mixture was stirred at room temperature for 24 hrs till the complete conversion of the compound of formula 5 to the compound of the formula 6. Excess of solvent was evaporated and the reaction mixture was diluted with 10 ml water and extracted with ethyl acetate, and solvent removed to furnish compound of formula 6, recovery 150 mg.

EXAMPLE (ii)

Preparation of (−)-methyl(2R,3S)-phenylglycidates of the formula 8 where R'=CH$_3$ It was prepared from 6 following the procedure given in step 'f' example (i) for compound 7. [ ]$_D^{25}$−153.0° (c,l, CHCl$_3$).

What is claimed is:

1. A stereoselective chemoenzymatic process for the synthesis of optically enriched trans alkyl phenylglycidate in its enantiomeric forms alkyl(2S,3R)-phenylglycidate and alkyl (2R,3S)-phenylglycidate of formulae 7 and 8

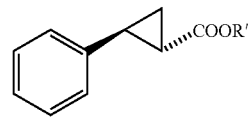

(7)

(2S,3R)

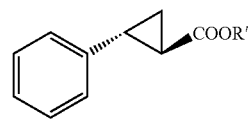

(8)

(2R,3S)

respectively, wherein said process comprises steps of,
  a. halogenating alkyl cinnamate of formula 1 by action of a halogenating agent to obtain halohydrins of formula 2, where X represents bromine or iodine, and R' represents C-1 to C-5 alkyl group;

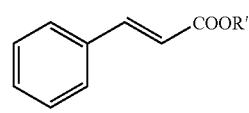

(1)

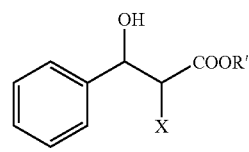

(2)

b. acylating the halohydrins of formula 2 using an acyl anhydride in presence of a base to trans alkyl 3-acyloxy-2-halo-3-phenylpropanoates of formula 3-;

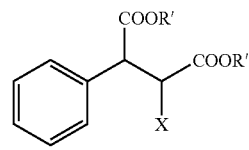

(3)

c. incubating the trans alkyl 3-acyloxy-2-halo-3-phenylpropanoates of formula 3 with dry powder of the lipase in an aqueous buffer phase optionally in presence of an organic medium at a temperature range of 10–40° C.

for the time duration in the range of 30–55 hr. to facilitate the reaction to get hydrolysed alkyl(2R,3R)-2-halo-3-hydroxy-3-phenylpropanoates of formula 4 and unhydrolysed alkyl(2S,3S)-3-acyloxy-2-halo-3-phenylpropanoates of formula 5;

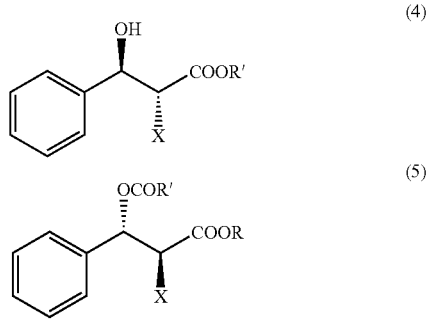

d. separating the hydrolysed alkyl(2R,3R)-2-halo-3-hydroxy-3-phenylpropanoates of formula 4 and unhydrolysed alkyl(2S,3S)-3-acyloxy-2-halo-3-phenylpropanoates of formula 5 by conventional method of chromatography;
e. incubating the optically enriched unhydrolised phenyl proponoates of formula 5 with crude dry powder of lipase from *Aspergillus niger* in an aqueous buffer phase in presence of an organic solvent to further improve the enantiopurity;
f. reacting the optically enriched products of formula 5 with an acid to furnish optically enriched alkyl(2S,3S) 2-halo-3-hydroxy-3-phenylpropanoate of formula 6, and

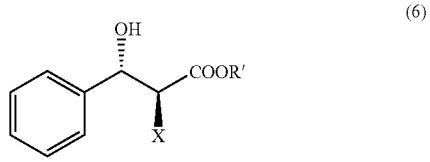

g. treating the compounds of formulae 4 and 6 with an alkali or an acid in an organic or aqueous phase which leads the formation of epoxide ring by cyclisation to furnish optically enriched alkyl(2S,3R)-phenylglycidate and alkyl(2R,3S)-phenylglycidate of formulae 7 and 8 respectively.

2. A process as claimed in claim 1, wherein the halogenating agent used for the preparation of trans halohydrin of formula 2 are selected from a group comprising N-halosuccinimide such as N-bromosuccinimide, N-iodosuccinimide or sodium bromate, periodic acid, 1,3-dibromo-5,5-dimethyl hydantoin, iodine and bromine.

3. A process as claimed in claim 2, wherein the halohydroxylation process is effected in aqueous phase, or in an organic phase, or in aqueous organic phase, where the organic phase comprises water miscible solvents.

4. A process as claimed in claim 3, wherein the halohydroxylation process is effected at a temperature between 0–60° C.

5. A process as claimed in claim 1 wherein the acylating agent is selected from acyl anhydrides, acyl chlorides.

6. A process as claimed in claim 1 wherein the base is selected from the group consisting of pyridine, and N,N-dimethyl aminopyridine (DMAP).

7. A process as claimed in claim 1 wherein enzyme lipase is from crude dry powder of *Aspergillus niger*.

8. A process as claimed in claim 1 wherein the crude dry powder of lipase from *Aspergillus niger* is used to effect the kinetic resolution.

9. A process as claimed in claim 1, wherein the aqueous phosphate buffer has the pH in the range of 5 to 7.5.

10. A process as claimed in claim 1, wherein stereospecific hydrolysis is most suitably carried out in presence of an organic cosolvent selected from the group consisting of hexane, toluene, dichloromethane, acetone, acetonitrile, dimethylformamide, dimethyl sulphoxide, methanol and ethanol, wherein the organic co-solvent is at 10–90% concentration.

11. A process as claimed in claim 1, wherein the stereospecific hydrolysis is effected suitably at a temperature of about 30° C.

12. A process as claimed in claim 1, wherein the incubation period is about 48 hours.

13. A process as claimed in claim, 1 wherein the cyclisation to optically enriched glycidate of formula 7 is effected in presence of an organic or inorganic base.

14. A process as claimed in claim 1 wherein the cyclisation is effected in the presence of an organic base selected from the group consisting of triethylamine, piperidine, 1,4-diazabicyclo[2,2,2]octane (DABCO), and 1,8-diazabicyclo [5,4,0]undec-7-ene (DBU).

15. A process as claimed in claim 1, wherein the cyclisation to optically enriched glycidate of formula 8 is effected most suitably in presence of an acid selected from the group consisting of hydrochloric acid, sulfuric acid or trifluoro acetic acid and boron trifluoride ($BF_3$).

16. A process as claimed in claim 1, wherein the product of the formula 7 has enantiomeric excess in the range of 86–95%.

17. A process as claimed in claim 1, wherein the product of the formula 8 has enantiomeric excess in the range of 60–99.5%.

18. A process as claimed in claim 3, wherein the organic phase is acetone, tetrahydrofuran, dioxane, dimethyl formamide, or methanol.

19. A process of claim 5, wherein the acylating agent is acetic anhydride; propionic anhydride, butyric anhydride or acyl chlorides thereof.

20. A process of claim 1, wherein the cyclisation to optically enriched gycidate of formula 7 is affected in the presence of sodium hydroxide, sodium carbonate or a combination thereof.

* * * * *